United States Patent [19]

Mussi et al.

[11] Patent Number: 4,912,058
[45] Date of Patent: Mar. 27, 1990

[54] ROLLER BOTTLE

[75] Inventors: Edward F. Mussi, Hewitt; Harry E. Gray, Bloomingdale, both of N.J.

[73] Assignee: Becton, Dickinson and Company, Franklin Lakes, N.J.

[21] Appl. No.: 344,318

[22] Filed: Apr. 27, 1989

[51] Int. Cl.[4] .............................................. C12M 3/00
[52] U.S. Cl. .................................... 435/285; 435/296; 366/233
[58] Field of Search ............... 435/285, 286, 296, 284, 435/300, 301, 297; 366/233, 234

[56] References Cited

U.S. PATENT DOCUMENTS

| | | | |
|---|---|---|---|
| 3,812,016 | 5/1974 | Muller | 195/139 |
| 3,853,712 | 12/1974 | House et al. | 195/127 |
| 3,941,661 | 3/1976 | Noteboom | 435/296 |
| 4,004,981 | 1/1977 | Hurni et al. | 195/127 |
| 4,046,138 | 9/1977 | Libman et al. | 435/296 |
| 4,065,359 | 12/1977 | Hurni | 195/127 |
| 4,289,248 | 9/1981 | Lynn | 215/330 |
| 4,314,030 | 2/1982 | Habich | 435/296 |
| 4,317,886 | 3/1982 | Johnson et al. | 435/285 |
| 4,337,104 | 6/1982 | Lynn | 435/296 |
| 4,600,694 | 7/1986 | Clyde | 435/312 |
| 4,689,301 | 8/1987 | Adet et al. | 435/284 |
| 4,829,004 | 5/1989 | Varani et al. | 435/285 |

Primary Examiner—James C. Yeung
Attorney, Agent, or Firm—Robert P. Grindle

[57] ABSTRACT

A roller bottle is provided with provision for increased internal surface area for cell growth by the use of a foamed, textured or woven liner or sleeve inserted into the bottle prior to use. The sleeve may be used in a single use roller bottle or a multiple use roller bottle. With the latter, the sleeve is discarded, the bottle sterilized, and a new sleeve or liner is inserted. The interstices of the foamed, textured or woven surface has the effect of increasing the actual surface area available for culturing cells in each single roller bottle, thus making the roller bottle of the invention cost effective.

10 Claims, 2 Drawing Sheets

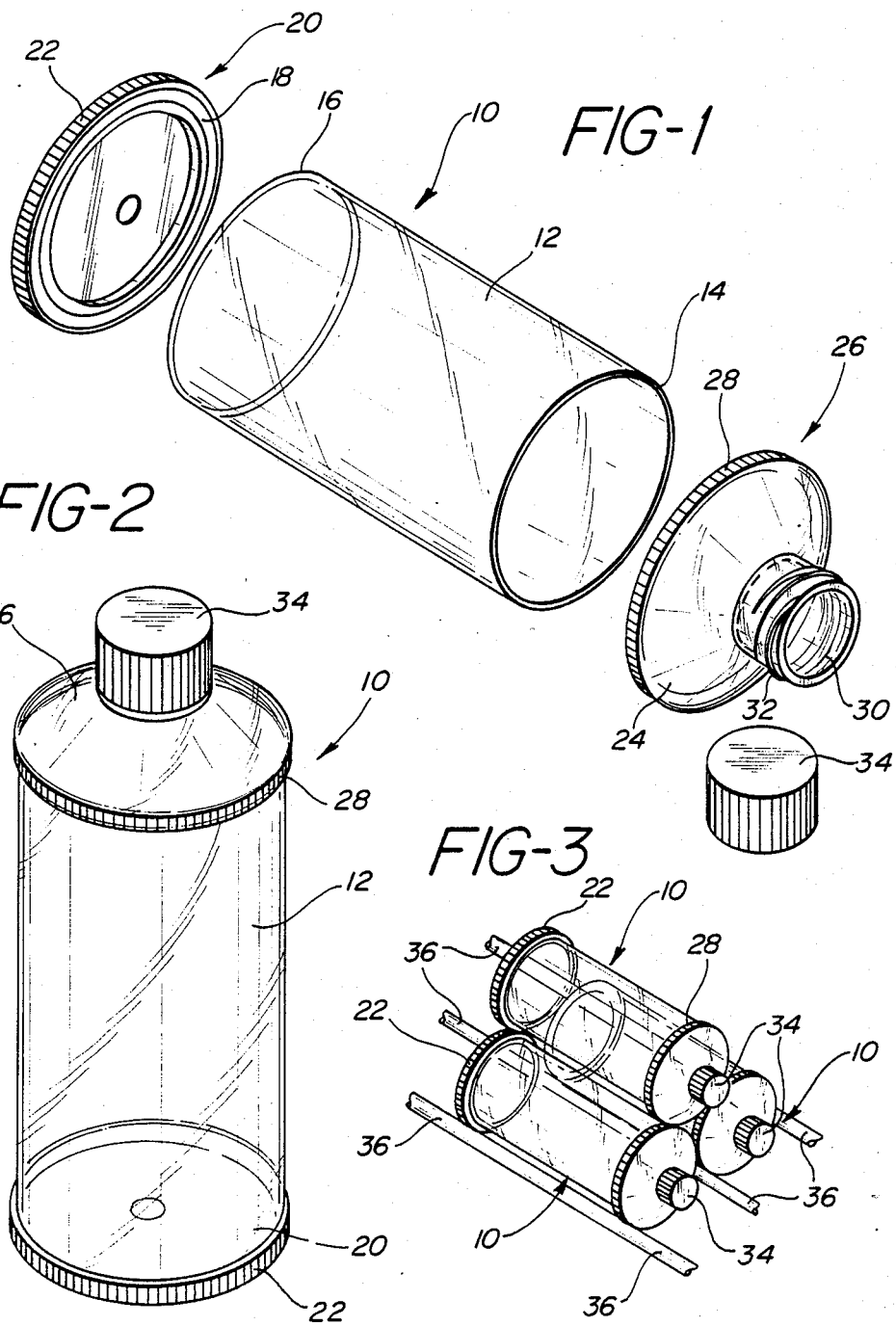

ROLLER BOTTLE

BACKGROUND AND STATEMENT OF THE INVENTION

The present invention relates to roller bottles for cell growth and production, and more particularly concerns a device having a greatly increased internal surface area of the roller bottle in order to achieve enhanced quantities of cells grown from a single roller bottle. The invention includes the utilization of a liner or a sleeve comprised of a foamed, woven or textured material. Also, the material may be microporous. Thus, the interstices or minute openings and surfaces formed in the texture, weave or foam of the sleeve or liner has the effect of increasing substantially the effective surface area on the internal surface of each roller bottle. For this reason, the invention provides a cost effective approach to the greatly increased number of roller bottles being utilized for cell growth.

The invention includes the utilization of the foamed microporous textured or woven sleeve of the invention in a single use roller bottle. With such an arrangement, the sleeve is inserted prior to the final welding or joining of the parts forming the roller bottle together. Alternatively, a reusable roller bottle may be utilized which may be opened for insertion of a sleeve of the invention sequentially for each use of the bottle. With such an arrangement, once the cells are harvested from a culturing stage in the use of the roller bottle, the sleeve is removed and discarded, and the roller bottle sterilized for subsequent use. After sterilization, of course, a new liner or sleeve is inserted for the additional use.

Containers which are used in the laboratory and like situations for culturing of cells are commonly known as "roller bottles." These roller bottles are generally cylindrically shaped and are adapted to rotate about their axes. The internal surfaces of such roller bottles are for providing active surfaces for the growth of cells. A liquid growth medium is introduced into the roller bottles. The rotating movement of the bottle keeps the internal surfaces wetted with the liquid medium, thereby encouraging the growth of cells. Rotating rollers in an appropriate apparatus are employed to rotate these roller bottles. Usually, the roller bottle apparatus, as is described below, is adapted to be placed inside an incubator or incubating room to control the temperature of cell growth inside the roller bottles.

As will be understood by practitioners-in-the-art, it is desirable to grow large amounts of cells, mostly for cell by-products, such as pharmaceutical substances that are secreted by cells; for example, insulin, interferon, urokinase or viral vaccines. The standard roller bottles have been successful in increasing the yield of cell growth in as much as the entire inside peripheral surface can be utilized for cell culturing.

In conceiving ways to increase the yield of growing cells in roller bottles, there are substantial constraints which have to be considered in suggesting improvements. In particular, roller bottle rotation devices are widely used in standard sizes and incubators. These devices are in place in many laboratories and are designed to accept roller bottles of a specific size and shape. Thus, to replace these would be expensive and cause substantial lack of standardization throughout the laboratory field.

The outside configuration or diameter of roller bottles is generally not one of the parameters which has changed to improve the yield of cells grown in roller bottles. Accordingly, improvements in roller bottles for increasing cell growth, for practical purposes, is limited to modifications of interior surfaces of the roller bottles, and/or improvements in harvesting the cells once they are grown.

One of the problems of the approaches which have taken place in the past has to do with the fact that involved mechanical improvements to roller bottles increase the cost thereof. Literally, thousands of roller bottles are used on a daily basis and are discarded, once they are used. Therefore, the cost of roller bottles must be decreased because of the vast increase in equipment and development costs for medical applications.

Various approaches have been used in order to increase the surface area internally of roller bottles. One approach is to increase the amount of actual surface available for cells to grow on. Representative prior art devices which increase the surface area internally of conventional roller bottles are U.S. Pat. No. 3,941,661, issued Mar. 2, 1976; U.S. Pat. No. 4,317,886, issued Mar. 2, 1982; and co-pending U.S. Application Ser. No. 204,796 filed June 10, 1988.

Another approach to increase the yield of cells developed internally of roller bottles includes the combination of increasing the surface area thereof, and the use of involved mechanical devices cooperating with these increased surfaces in order to remove a greater harvest of cells once they are developed on the increased surface internally of the bottles. Representative of these devices include those taught and claimed in U.S. Pat. No. 4,004,981 issued Jan. 25, 1987; U.S. Pat. No. 4,065,359 issued Dec. 27, 1977; and U S. Pat. No. 4,600,694 issued July 15, 1986.

While each of the above three patents have the effect of increasing the surface area internally of roller bottles and increasing the yield of cells removed therefrom, the internal device utilized in these patents in the arrangements for scraping the cells from the increased surface areas are very involved, and increase the cost of the individual roller bottles, and the product derived therefrom, substantially. Moreover, these are not single-use devices and have been used largely in the labs where they originated.

With this invention, by contrast, a device is provided for roller bottles which is inserted into the roller bottles in tee form of a liner or sleeve which increases the actual surface area useful for cell growth thereon. The sleeve or liner is comprised of a foamed, textured or woven material which provides minute surfaces surrounding the interstices forming the texture, weave and/or foamed characteristics of the sleeve or liner of the invention.

Because of this, the actual surfaces involved for cell growth include areas positioned at planes diverging from the general plane of the liner or sleeve of the invention. For this reason, each roller bottle has a substantial increase in cell growth production area or surface for each use of the bottle.

The invention contemplates, as one embodiment, the use of the sleeve or liner of the invention in a single-use roller bottle. That is, the sleeve or liner is inserted into the formed bottle prior to the top or cap of the roller bottle being welded into place on the cylindrical body portion of the roller bottle. Thus, the roller bottle is used a single time, cells are grown on the surfaces thereof, and the cells are thereafter removed and the roller bottle thrown away.

Alternatively, the sleeve or liner of the invention may be used in a multiple or repeat use roller bottle. That is, the roller bottle may have one or both ends screwed onto or otherwise removably attached to the cylindrical body portion of the roller bottle. This provides access to the internal area of the roller bottle for repeat insertion of one of the liners or sleeves of the invention. Thus, once the roller bottle is used, and cells are developed or cultured on the internal surface of the roller bottle on the interstices and uneven areas of the liner of the invention, the cells are harvested and the top or bottom or both are removed from the used roller bottle and the used liner is removed and discarded. Thereafter, the parts forming the roller bottle are sterilized and a new liner is inserted for subsequent use of the same roller bottle.

In viewing generally the conditions for producing roller bottles in accordance with this invention, a variety of thermoplastic materials may be utilized, including, for example, polystyrene, polyethylene terephthalate, the polyolefins, polyurethane and polyvinyl chloride. These materials are representative of materials which would be utilized for the single-use form of roller bottle utilizing the sleeve or liner of the invention here. Such a single-use roller bottle may be blow molded, as will be understood by practitioners-in-the-art, which reduces the cost of the individual roller bottles produced in accordance herewith.

Alternatively, if a reusable roller bottle is to be formed in accordance with this invention, the materials selected for such repeat use must be comprised of a material which will tolerate repeated sterilization procedures. Materials which may be used include, for example, glass, stainless steel or certain resins which tolerate the conditions necessary for sterilization. Of course, reusable bottles allow considerable cost savings to the end user, because the disposable inserts of the invention are cheaper than the cost of purchasing a new roller bottle.

The inserts of the invention may be made from a variety of materials which improve cell growth surface area. Polyethylene terephthalate, polyurethane and certain papers having the appearance or property of "woven" characteristics may be utilized for the inserts. Whereas these materials were not desirable in the past because of their poor structural properties in a foamed, woven, microporous or textured format, by utilizing them as liners or sleeves in a separate roller bottle provides the support required for these materials which are, otherwise, desirable for cell growth surfaces.

Representative specific materials which may be used for the sleeves or liners of the invention include microporous materials such as polypropylene, ultrahigh molecular weight polyethylene, high density polyethylene and styrene arrylonitrile, all of which may be obtained from either Porex Technologies, 500 Bohannon Road, Fairburn, Ga. 30213, or Chromex Corporation, 19 Clay Street, Brooklyn, N.Y. 11222. A further representative material is foamed polyurethaneether which may be obtained from W. R. Grace, Organic Chemical Division, 55 Hayden Avenue, Lexington, Mass. 02173.

As further exemplary of materials which may comprise the sleeve or liner of the invention is textured or woven paper such as 40 pound basis weight medical grade paper supplied by James River Corporation, 100 Island Avenue, Parchment, Mich. 49004-1391 or 42 pound basis weight medical grade paper supplied by CPM Incorporated, P.0. Box 1280, 131 Sullivan Street, Claremont, N.H. 03743.

In addition, non-woven fabrics or composites may be used such as spun-bonded polyester which may be obtained from Eaton-Dikeman, P.0. Box A, Mount Holly Springs, Pa. 17065-0238.

Other objects and advantages of this invention will be apparent from the following description, the accompanying drawings and the appended claims.

DESCRIPTION OF THE DRAWINGS

FIG. 1 is an exploded view of one embodiment of roller bottle utilized in the invention;

FIG. 2 is a perspective view of the assembled bottle of FIG. 1;

FIG. 3 is a perspective view of a roller bottle assembly apparatus illustrating how bottles are arranged and rotated during use in such an apparatus;

DETAILED DESCRIPTION OF THE INVENTION

Figure 4:
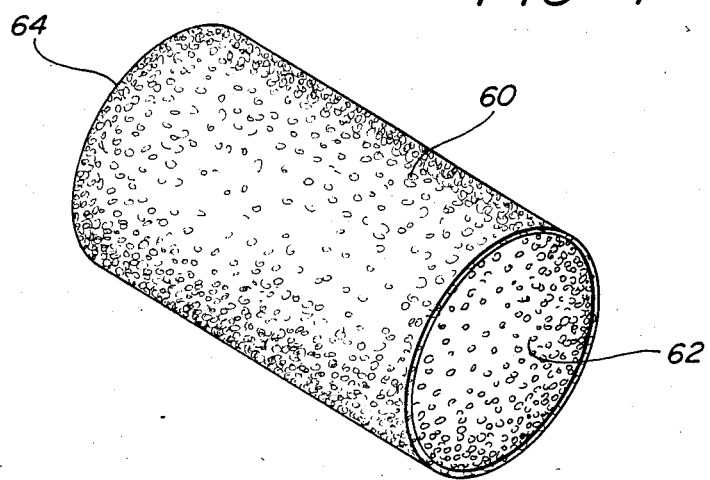
FIG. 4 is a perspective view of a sleeve or liner of the invention.

Referring to the drawings in which like reference characters refer to like parts throughout the several views thereof, an exploded view of roller bottle generally designated 10 is shown. The roller bottle includes a cylindrical body 12 comprised of a transparent material for making proper observation of the internal area of the roller bottle during and after use. Generally, in this connection, it is desirable that all roller bottles are comprised of a clear or transparent material for observation of the contents thereof. However, it will be understood in connection with this invention, that once a liner or sleeve of the invention is inserted into the roller bottle, that the actual internal contents of the roller bottle will not be available for observation other than, perhaps, through the transparent top or bottom wall of the roller bottle.

It should be understood, further, that the sleeve or liner, once it is inserted into the formed roller bottle may be treated prior to the top being molded onto the final roller bottle formation. That is, the interior surfaces of the formed roller bottle may be tissue culture treated by and of several known methods such as corona discharge, liquid coating, or ozone injection prior to assembly.

Referring further to the embodiment shown in FIG. 1, one end 16 of the tubular body portion 12 of the invention is inserted into an annular groove 18 of bottom end cap 20. Cap 20 includes a serrated rim 22. If the embodiment, as is shown in FIG. 1, is to result in a single-use bottle, the two parts may then be permanently joined by ultrasonic welding, gluing or spin welding or the like. Alternatively, if the bottle is to be a reusable bottle, the end 16 may be joined onto the bottom part 20 in order to gain subsequent access to that end of the container. The parts may be press-fit, as shown, or cooperating screw threads may be utilized, for example.

However, if the container is glass, the bottom portion 20 and the cylindrical portion 12 may be molded as a single glass part.

The top cap 26 has a serrated rim 28, similar to that of the bottom cap 20 and is somewhat conical in shape. It is provided with an integral, substantially smaller diameter neck having integral external screw threads 32, for receiving thereon a closure cap 34 which, as will be understood has mating internal threads for cooperating with threads 32. Cap 34 has a serrated exterior surface to facilitate gripping by the user. It is within the purview of this invention that cap 34 and neck 30 include an intermediate positioning arrangement to allow access of the incubating humid environment for proper cell growth environment. Such an arrangement is taught and claimed in U.S. Pat. No. 4,289,248 which is incorporated herein by reference, in its entirety.

Again, if the embodiment is to be a reusable one as shown in the assembled position in FIG. 2, cooperating screw threads, not shown, may be used for cap 26 fitting on the open end 14 of the cylindrical body portion 12. Alternatively, this can be a press-fit connection as long as the desired non-leaking joint is obtained.

As discussed above, the roller bottles are utilized in an apparatus where a plurality of such bottles are rotated in a cell culture environment for a period of time. Representative of such apparatus is that shown in FIG. 3. As can be seen, the bottles may be stacked as shown in FIG. 3 such that the serrated portions such as 22, 28 shown in FIGS. 1 and 2 may cooperate with each other on the individual bottles for rotating a plurality of bottles simultaneously.

It will be observed that if the lower bottles in FIG. 3 are rotated in a clockwise direction, then the upper bottle having serrated rims which mesh with those of the lower bottles will rotate in a counterclockwise direction. At any rate, many more bottles than are shown in the drawing can be stacked in the manner shown thereby increasing the capacity of the roller apparatus.

As a feature of the invention here, each one of those stacked bottles have an increased surface area for the actual culturing environment internally of each one of the roller bottles. Thus, the liners or sleeves of the invention increase substantially the effective internal surface area for cell growth culturing for each individual bottle.

Referring now to FIG. 4, a representative foamed sleeve 60 is shown which, as stated above, may be, for example, a polyurethane foam. The sleeve 60 has open ends 62, 64 at opposite ends thereof. It will be understood by practitioners-in-the-art in forming such sleeves, that the end 64 may be, for example, closed so that a cylindrical closed end sleeve is provided for insertion into a roller bottle.

Figure 5:
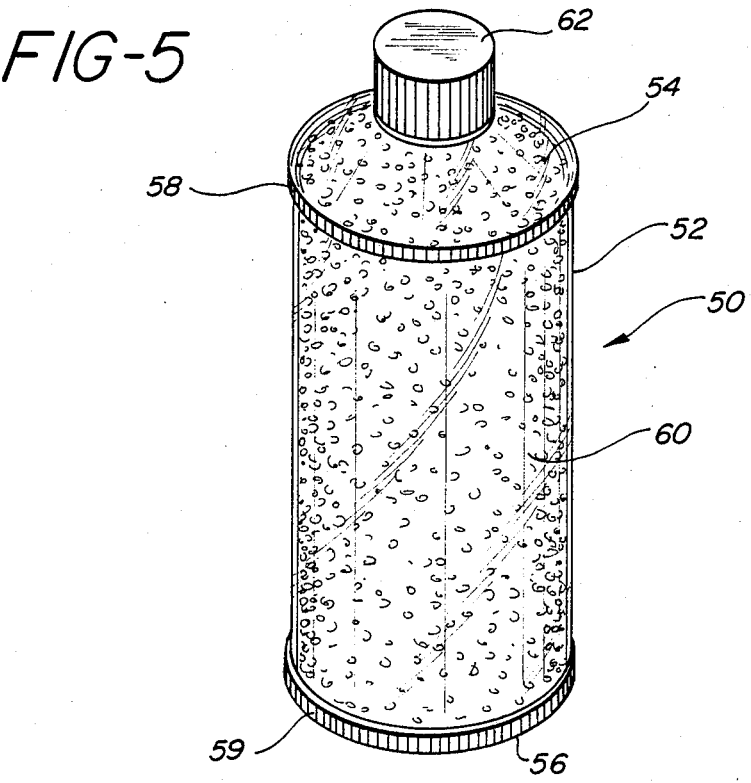
FIG. 5 is a perspective view of another embodiment of the invention illustrating a single-use roller bottle with the liner of the invention contained therein.

Referring now to FIG. 5, a representative single-use roller bottle is shown. That is, roller bottle 50 includes a cylindrical body portion 52, a cap 54 having a serrated rim 58 and a bottom cap 56 having a serrated rim 59. The container 50 shown in FIG. 5 includes a cap 62 cooperating with the neck of container 50. In the formation of the arrangement shown in FIG. 5, which is a single-use arrangement, a sleeve 60 is inserted prior to the joining of the cap 54 to the cylindrical body portion 52. Since the closure is a permanent closure, the two parts may be joined together by, for example, sonic welding if the parts are comprised of a plastic material for that purpose. Otherwise, the parts may be joined together by the use of a glue or they may be press-fit, depending upon the material being utilized for the container, and as long as the connection is properly sealed against leakage.

Thus, as will be appreciated from the above, there is provided in accordance with this invention, a simplified one-piece unitary roller bottle having a greatly increased surface area for cell growth formation therein simply by the utilization of a separately formed sleeve which may be formed in substantial number at greatly reduced cost. Thus, a reusable glass bottle may be used many times with relatively inexpensive sleeves.

By the same token, if the roller bottle is to be used a single time, a relatively inexpensive resin material with the cooperating sleeve of the invention inserted therein may be used. With that arrangement, as will be understood, because of this substantially increased surface area useful for cultivating cells in the internal area of the bottle, the bottle is much more cost effective. As will be understood, with either embodiment used here, mass production techniques are readily available for reducing the cost thereof.

While the forms of apparatus herein described constitute preferred embodiments of the invention, it is to be understood that the invention is not limited to these precise forms of apparatus and that changes may be made therein without departing from the scope of the invention which is defined in the appended claims.

For example, roller bottles of different lengths may be produced, in accordance with roller bottle apparatus requirements already in existence. These modifications may be made without any expensive reassembly provisions in order to produce the roller bottles. Thus, mass production techniques may be used in a simplified form to produce many roller bottles of the kind to which this invention is directed.

What is claimed is:

1. A roller bottle for cell growth culturing, characterized by
    (a) a substantially cylindrical housing open at both ends, and defining a hollow cell growth chamber in said roller bottle;
    (b) a bottom end cap for closing one end of said housing;
    (c) a top cap for closing the end of said housing opposite said bottom cap;
    (d) an opening positioned centrally of said top cap for gaining access to said cell growth chamber;
    (e) a closure cap for closing said opening in said top cap;
    (f) first cooperating joining means on said housing and said bottom end cap for joining said bottom end cap to said housing;
    (g) second cooperating joining means on said housing and said top cap for joining said top cap to said housing; and
    (h) a liner comprised of a single layer sleeve for lining the walls of said hollow growth chamber;
    (i) said liner comprised of a material presenting a textured uneven surface to increase the effective surface area for cell growth in said chamber.

2. The roller bottle of claim 1, further characterized by
    (a) said roller bottle is a single-use roller bottle;
    (b) said liner is inserted into said chamber prior to the closing of at least one of the open ends thereof; and
    (c) said first and second joining means are permanent connections.

3. The roller bottle of claim 1, further characterized by
    (a) said roller bottle is a repeated use roller bottle;

(b) a plurality of said liners are inserted sequentially into said chamber for each use of said roller bottle; and (c) said first and second joining means are disconnectable for removing one or both of said bottom end cap and said top end cap.

4. The roller bottle of claim 1, further characterized by (a) said liner is selected from the group consisting of microporous polyvinyl chloride, microporous polyethylene terephthalate, microporous polypropylene, microporous ultrahigh molecular weight polyethylene, microporous high density polyethylene, microporous styrene acrylonitrile, foamed polyurethane-ether, 40 pound basis weight medical grade paper, 42 pound basis weight medical grade paper, and spun-bonded resin.

5. The roller bottle of claim 2, further characterized by (a) said roller bottle is comprised of a material selected from the group consisting of microporous polyvinyl chloride, microporous polyethylene terephthalate, microporous polypropylene, microporous ultrahigh molecular weight polyethylene, microporous high density polyethylene, microporous styrene acrylonitrile, foamed polyurethane-ether, 40 pound basis weight medical grade paper, 42 pound basis weight medical grade paper, and spun-bonded resin.

6. The roller bottle of claim 3, further characterized by (a) said roller bottle is comprised of a material selected from the group consisting of glass, stainless steel and thermoplastic resin.

7. The roller bottle of claim 1, further characterized by (a) each of said top cap and bottom cap having a serrated rim enabling said roller bottle to provide cooperating relative rotation with the serrated rims of other roller bottles in a roller bottle apparatus.

8. A liner for use in a roller bottle, characterized by (a) a cylindrical liner body comprised of a single layer for lining the internal surface of a roller bottle;

(b) said body defining a hollow liner chamber therein;

(c) the walls of said hollow liner chamber being textured and uneven for presenting an increase in effective cell growth surface area in said hollow liner chamber; and (d) said liner being inserted into a roller bottle prior to final closure thereof.

9. The liner of claim 8, further characterized by (a) one end of said cylindrical liner body being closed; and (b) said closed end of said cylindrical liner body covering the bottom end of a roller bottle into which said liner body is inserted.

10. The liner of claim 8, further characterized by (a) said liner comprised of a material selected from the group consisting of microporous polyvinyl chloride, microporous polyethylene terephthalate, microporous polypropylene, microporous ultrahigh molecular weight polyethylene, microporous high density polyethylene, microporous styrene acrylonitrile, foamed polyurethane-ether, 40 pound basis weight medical grade paper, 42 pound basis weight medical grade paper, and spun-bonded resin.

* * * * *